(12) United States Patent
Gyory

(10) Patent No.: US 10,814,062 B2
(45) Date of Patent: Oct. 27, 2020

(54) RESERVOIR WITH LOW VOLUME SENSOR

(71) Applicant: Becton, Dickinson and Company, Franklin Lakes, NJ (US)

(72) Inventor: J. Richard Gyory, Sudbury, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 363 days.

(21) Appl. No.: 15/692,887

(22) Filed: Aug. 31, 2017

(65) Prior Publication Data
US 2019/0060565 A1 Feb. 28, 2019

(51) Int. Cl.
*A61M 5/148* (2006.01)
*A61M 5/168* (2006.01)
*A61M 5/142* (2006.01)

(52) U.S. Cl.
CPC ............ *A61M 5/168* (2013.01); *A61M 5/148* (2013.01); *A61M 5/14216* (2013.01); *A61M 5/14248* (2013.01); *A61M 2205/18* (2013.01); *A61M 2205/3306* (2013.01); *A61M 2205/3317* (2013.01); *A61M 2205/3386* (2013.01); *A61M 2205/50* (2013.01); *A61M 2205/581* (2013.01); *A61M 2205/582* (2013.01); *A61M 2205/587* (2013.01); *A61M 2205/702* (2013.01); *A61M 2205/8206* (2013.01)

(58) Field of Classification Search
CPC .............. A61M 5/168; A61M 5/14216; A61M 5/14248; A61M 5/14212; A61M 2205/3386; A61M 2205/3306; A61M 2205/3317; A61M 2205/18; A61M 2205/587; A61M 2205/581; A61M 2205/582
See application file for complete search history.

(56) References Cited

U.S. PATENT DOCUMENTS

| | | |
|---|---|---|
| 4,596,575 A | 6/1986 | Rosenberg et al. |
| 5,149,413 A | 9/1992 | Maget |
| 5,395,324 A | 3/1995 | Hinrichs et al. |
| 5,957,891 A | 9/1999 | Kriesel et al. |
| 6,085,574 A | 7/2000 | Neftel et al. |
| 6,120,665 A | 9/2000 | Chiang et al. |
| 6,174,675 B1 | 1/2001 | Chow et al. |
| 6,186,982 B1 | 2/2001 | Gross et al. |
| 6,460,420 B1 | 10/2002 | Paul et al. |

(Continued)

FOREIGN PATENT DOCUMENTS

| | | |
|---|---|---|
| EP | 2179755 | 4/2010 |
| EP | 2196231 B1 | 2/2013 |

(Continued)

*Primary Examiner* — Laura A Bouchelle
*Assistant Examiner* — Anh Bui
(74) *Attorney, Agent, or Firm* — Dickinson Wright PLLC

(57) ABSTRACT

A medical device with a volume sensor is provided for administering liquid drug therapy to a user. The medical device comprises a flexible reservoir for housing a supply of a liquid drug, a rigid structure with a chamber and a side hole in fluid communication with the flexible reservoir, a plunger mounted inside the chamber and configured to seal one side of the chamber, and a switch implemented to indicate the position of the plunger. When the inside end of the plunger passes the side hole, the switch is activated to transmit a signal indicating liquid volume in the flexible reservoir.

14 Claims, 6 Drawing Sheets

(56) References Cited

U.S. PATENT DOCUMENTS

| | | |
|---|---|---|
| 6,485,461 B1 | 11/2002 | Mason et al. |
| 6,656,159 B2 | 12/2003 | Flaherty |
| 6,689,108 B2 | 2/2004 | Lavi et al. |
| 6,723,068 B2 | 4/2004 | Lavi et al. |
| 6,805,841 B2 | 10/2004 | Shvets et al. |
| 6,842,782 B1 | 1/2005 | Malik et al. |
| 7,018,360 B2 | 3/2006 | Flaherty et al. |
| 7,063,778 B2 | 6/2006 | Mpholo et al. |
| 7,081,189 B2 | 7/2006 | Squires et al. |
| 7,213,473 B2 | 5/2007 | Mosier et al. |
| 7,267,753 B2 | 9/2007 | Anex et al. |
| 7,431,052 B2 | 10/2008 | Gravesen et al. |
| 7,465,382 B2 | 12/2008 | Paul et al. |
| 7,481,792 B2 | 1/2009 | Gonnelli et al. |
| 7,517,440 B2 | 4/2009 | Anex et al. |
| 7,521,140 B2 | 4/2009 | Arnold et al. |
| 7,632,247 B2 | 12/2009 | Adams |
| 7,654,127 B2 | 2/2010 | Krulevitch et al. |
| 7,686,787 B2 | 3/2010 | Moberg et al. |
| 7,691,244 B2 | 4/2010 | Levitan et al. |
| 7,708,873 B2 | 5/2010 | Bazant et al. |
| 7,753,656 B2 | 7/2010 | Lemoff et al. |
| 7,815,609 B2 | 10/2010 | Hines et al. |
| 7,875,159 B2 | 1/2011 | Anex et al. |
| 7,887,508 B2 | 2/2011 | Meng et al. |
| 7,896,865 B2 | 3/2011 | Kulessa |
| 7,896,867 B2 | 3/2011 | Gordon et al. |
| 7,918,825 B2 | 4/2011 | O'Connor et al. |
| 7,938,801 B2 | 5/2011 | Hawkins et al. |
| 7,976,505 B2 | 7/2011 | Hines et al. |
| 7,981,106 B2 | 7/2011 | Gilad |
| 8,113,244 B2 | 2/2012 | Kamen et al. |
| 8,141,601 B2 | 3/2012 | Fehr et al. |
| 8,162,923 B2 | 4/2012 | Adams et al. |
| 8,202,260 B2 | 6/2012 | Mann et al. |
| 8,281,656 B2 | 10/2012 | Schnidrig |
| 8,409,151 B2 | 4/2013 | Hawkins et al. |
| 8,434,528 B2 | 5/2013 | Ibranyan et al. |
| 8,435,212 B2 | 5/2013 | Grigorov |
| 8,491,570 B2 | 7/2013 | Kamen et al. |
| 8,505,833 B2 | 8/2013 | Fehr et al. |
| 8,540,673 B2 | 9/2013 | Hines et al. |
| 8,602,067 B2 | 12/2013 | Kuhni et al. |
| 8,603,034 B2 | 12/2013 | Lynch et al. |
| 8,603,051 B2 | 12/2013 | Kuo et al. |
| 8,667,996 B2 | 3/2014 | Gonnelli et al. |
| 8,684,991 B2 | 4/2014 | Wyss |
| 8,690,855 B2 | 4/2014 | Alderete, Jr. et al. |
| 8,715,177 B2 | 5/2014 | Rao et al. |
| 8,740,847 B2 | 6/2014 | Levesque et al. |
| 8,821,442 B2 | 9/2014 | Haar |
| 8,827,976 B2 | 9/2014 | Studer |
| 8,858,511 B2 | 10/2014 | Gonnelli et al. |
| 8,876,802 B2 | 11/2014 | Grigorov |
| 8,894,612 B2 | 11/2014 | Hawkins et al. |
| 8,900,188 B2 | 12/2014 | Blumberg, Jr. et al. |
| 8,920,376 B2 | 12/2014 | Caffey et al. |
| 8,992,478 B2 | 3/2015 | Levesque |
| 9,039,653 B2 | 5/2015 | Chong et al. |
| 9,061,097 B2 | 6/2015 | Holt et al. |
| 9,089,475 B2 | 7/2015 | Fangrow |
| 9,089,637 B2 | 7/2015 | Chong et al. |
| 9,089,647 B2 | 7/2015 | Haenggi et al. |
| 9,446,193 B2 | 9/2016 | Geipel et al. |
| 2002/0123719 A1 | 9/2002 | Lavi et al. |
| 2003/0135159 A1 | 7/2003 | Daily et al. |
| 2004/0015134 A1 | 1/2004 | Lavi et al. |
| 2004/0059316 A1 | 3/2004 | Smedegaard |
| 2004/0068224 A1 | 4/2004 | Couvillon, Jr. et al. |
| 2006/0200112 A1 | 9/2006 | Paul |
| 2007/0282269 A1 | 12/2007 | Carter et al. |
| 2009/0026146 A1 | 1/2009 | Carlisle et al. |
| 2009/0156989 A1 | 6/2009 | Carter et al. |
| 2009/0259176 A1 | 10/2009 | Yairi |
| 2010/0049128 A1 | 2/2010 | McKenzie et al. |
| 2010/0234824 A1 | 9/2010 | Christoph et al. |
| 2011/0062703 A1 | 3/2011 | Lopez et al. |
| 2011/0190694 A1 | 8/2011 | Lanier, Jr. et al. |
| 2011/0306931 A1 | 12/2011 | Kamen et al. |
| 2012/0000569 A1 | 1/2012 | Wiegel |
| 2012/0010594 A1 | 1/2012 | Holt et al. |
| 2012/0041427 A1 | 2/2012 | Caffey et al. |
| 2012/0150139 A1 | 6/2012 | Studer |
| 2012/0277716 A1 | 11/2012 | Ali et al. |
| 2013/0006216 A1 | 1/2013 | Taylor et al. |
| 2013/0158501 A1 | 6/2013 | Arnitz |
| 2013/0226092 A1 | 8/2013 | Hawkins et al. |
| 2013/0303990 A1 | 11/2013 | Lynch et al. |
| 2013/0306191 A1 | 11/2013 | Metzmaker et al. |
| 2013/0319576 A1 | 12/2013 | Kavazov |
| 2013/0327413 A1 | 12/2013 | Chong et al. |
| 2013/0338597 A1 | 12/2013 | McAllister |
| 2014/0039396 A1* | 2/2014 | Geipel ............... A61M 5/14216 604/152 |
| 2014/0088555 A1 | 3/2014 | Li et al. |
| 2014/0090746 A1 | 4/2014 | Kuehni et al. |
| 2014/0124092 A1 | 5/2014 | Gonnelli et al. |
| 2014/0142535 A1 | 5/2014 | Imhof et al. |
| 2014/0163521 A1 | 6/2014 | O'Connor |
| 2014/0180238 A1 | 6/2014 | Imhof et al. |
| 2014/0336614 A1 | 11/2014 | Amirouche et al. |
| 2014/0373968 A1 | 12/2014 | Mueller |
| 2015/0011855 A1 | 1/2015 | Burnett et al. |
| 2015/0051571 A1 | 2/2015 | Lanigan et al. |
| 2015/0126934 A1 | 5/2015 | Chong et al. |
| 2015/0151041 A1 | 6/2015 | Yodfat et al. |
| 2015/0165115 A1 | 6/2015 | Gonnelli et al. |
| 2015/0174007 A1 | 6/2015 | Rodriguez et al. |
| 2016/0184514 A1 | 6/2016 | Kamen et al. |
| 2017/0000946 A1* | 1/2017 | Boyle .................. A61M 5/172 |
| 2017/0034950 A1* | 2/2017 | Sung ........................ G06F 1/20 |
| 2018/0117244 A1 | 5/2018 | Jugl et al. |

FOREIGN PATENT DOCUMENTS

| | | |
|---|---|---|
| WO | WO-2013096713 A2 | 6/2013 |
| WO | 2014194183 A3 | 6/2015 |

\* cited by examiner

RESERVOIR WITH LOW VOLUME SENSOR

FIELD OF THE INVENTION

The present invention relates generally to a reservoir for delivering liquid. A specific embodiment of the invention relates to a flexible reservoir with a low volume sensor for delivering liquid medicinal products, such as insulin. An additional embodiment provides a method for operating a flexible reservoir with a low volume sensor including providing a warning that replacement of the flexible reservoir is needed.

BACKGROUND OF THE INVENTION

Diabetes is a group of diseases characterized by high levels of blood glucose resulting from the inability of diabetic patients to maintain proper levels of insulin production when required. Persons with diabetes will require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

For the treatment of type 1 diabetes, there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy in which an insulin pump is used. The insulin pump can provide continuous infusion of insulin to a diabetic patient at varying rates in order to more closely match the functions and behavior of a properly operating pancreas of a non-diabetic person that produces the required insulin, and can help the diabetic patient maintain his/her blood glucose level within target ranges based on the diabetic patient's individual needs.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of a user. By contrast, a patch pump is an integrated device that combines most or all of the fluidic components, including the fluid reservoir, pumping mechanism and a mechanism for automatically inserting the cannula, in a single housing which is adhesively attached to an infusion site on the patient's skin, and does not require the use of a separate infusion or tubing set. Some patch pumps may wirelessly communicate with a separate controller (as in one device sold by Insulet Corporation under the brand name OmniPod®), while others are completely self-contained. Such devices are replaced on a frequent basis, such as every three days, when the insulin reservoir is exhausted.

As a patch pump is designed to be a self-contained unit that is worn by the diabetic patient, it is preferable to be as small as possible so that it does not interfere with the activities of the user. However, in order to minimize the overall size of the patch pump, its constituent parts should be reduced in size as much as possible. One such part is the reservoir for containing the insulin.

A conventional rigid reservoir, such as a syringe pump, controls the position of a plunger to dispense liquid. A major constraint of such a mechanism is the size of the system because it needs to accommodate both the length of the reservoir and the length of the plunger. Thus, a conventional rigid reservoir is difficult to deploy in a compact configuration. According, a need exists for an improved reservoir that can be efficiently deployed in a compact configuration to further reduce the overall size of a patch pump.

Low liquid level detection in the reservoir is important to ensure that the patch pump system functions correctly and/or to signal the need for replacement of the reservoir or patch pump. Various fill level detection systems have been proposed for various different applications. Currently, there are two principal methods for fill level detection. One provides electrical contacts points for metering doses. The other implements contactless fill level detection using capacitance measurement.

There are many advantages of conventional fill level detection systems when the flow rate and fill level need to be constantly monitored and/or adjusted. Conventional fill level detection systems provide accurate fill level data constantly or at a plurality of time points. Such systems are well suited where constant monitoring and adjustment is necessary. When only a low volume warning is needed to signal the need for replacement of the reservoir, a system with fill level detection function is unnecessarily more costly and more complicated.

An approach to reduce the overall size of a patch pump is to replace the syringe-type dosing mechanism by a downstream pump system drawing from a fluid reservoir. In such a device, a miniaturized pump is arranged downstream of the fluid reservoir to produce a negative pressure gradient that conveys the fluid from the reservoir to its destination. The miniaturized pump can alternatively be arranged to produce a positive pressure gradient that conveys the fluid from another larger fluid source into the reservoir to fill the reservoir.

Accordingly, there is a need in the art for providing a compact and more cost-effective reservoir with a low volume detector for warning of the need to replace the reservoir, so that many more diabetes patients can benefit from the advantages that patch pump devices provide.

SUMMARY OF THE INVENTION

It is an object of exemplary embodiments of the present invention to provide a flexible liquid reservoir with a low volume detector. It is a further object of the exemplary embodiments of the present invention to provide a notification of low liquid level in the flexible reservoir.

According to one aspect of the present invention, there is provided a medical device for administering liquid drug therapy to a user with a low volume sensor, said medical device comprising a flexible reservoir for containing a supply of a liquid drug, a rigid structure with a chamber and a side hole in fluid communication with the flexible reservoir, a plunger mounted inside the chamber and configured to seal one side of the chamber and a sensor for detecting low liquid volume in the flexible reservoir, wherein, when the inside end of the plunger passes the side hole, the sensor is activated to transmit a signal indicating low liquid volume in the flexible reservoir.

A third aspect of the present invention provides a method for a method for detecting low liquid volume and notifying a user of time-to-empty in a system comprising a pump mechanism, a flexible reservoir for housing a supply of a liquid drug, a rigid structure with a chamber and a side hole in fluid communication with the flexible reservoir, a plunger mounted inside the chamber and configured to seal one side of the chamber, a sensor for detecting low liquid volume in the flexible reservoir, and a control module in functional connection with the pump mechanism for controlling the operation of the pump mechanism, wherein when the inside end of the plunger passes the side hole, the sensor is activated to transmit a signal indicating low liquid volume in the flexible reservoir, the method comprising the steps of providing the rigid structure with the chamber connected to the flexible reservoir, applying a negative pressure to an end of the rigid structure, removing fluid from the flexible reservoir, detecting moment that the plunger loses contact with the switch, calculating estimated time for empty based on current flow rate and volume of the chamber and the conduit, alerting the user that volume is low and notifying user of approximate time when system will run out of liquid.

Other objects, advantages and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings, in which.

Throughout the drawings, like reference numerals will be understood to refer to like elements, features and structures.

DETAILED DESCRIPTION OF EXEMPLARY EMBODIMENTS

The matters exemplified in this description are provided to assist in a comprehensive understanding of exemplary embodiments of the invention, and are made with reference to the accompanying drawings. Those of ordinary skill in the art will recognize that various changes and modifications in the exemplary embodiments described herein can be made without departing from the scope and spirit of the claimed invention. Also, descriptions of well-known functions and constructions are omitted for clarity and conciseness.

Figure 1:
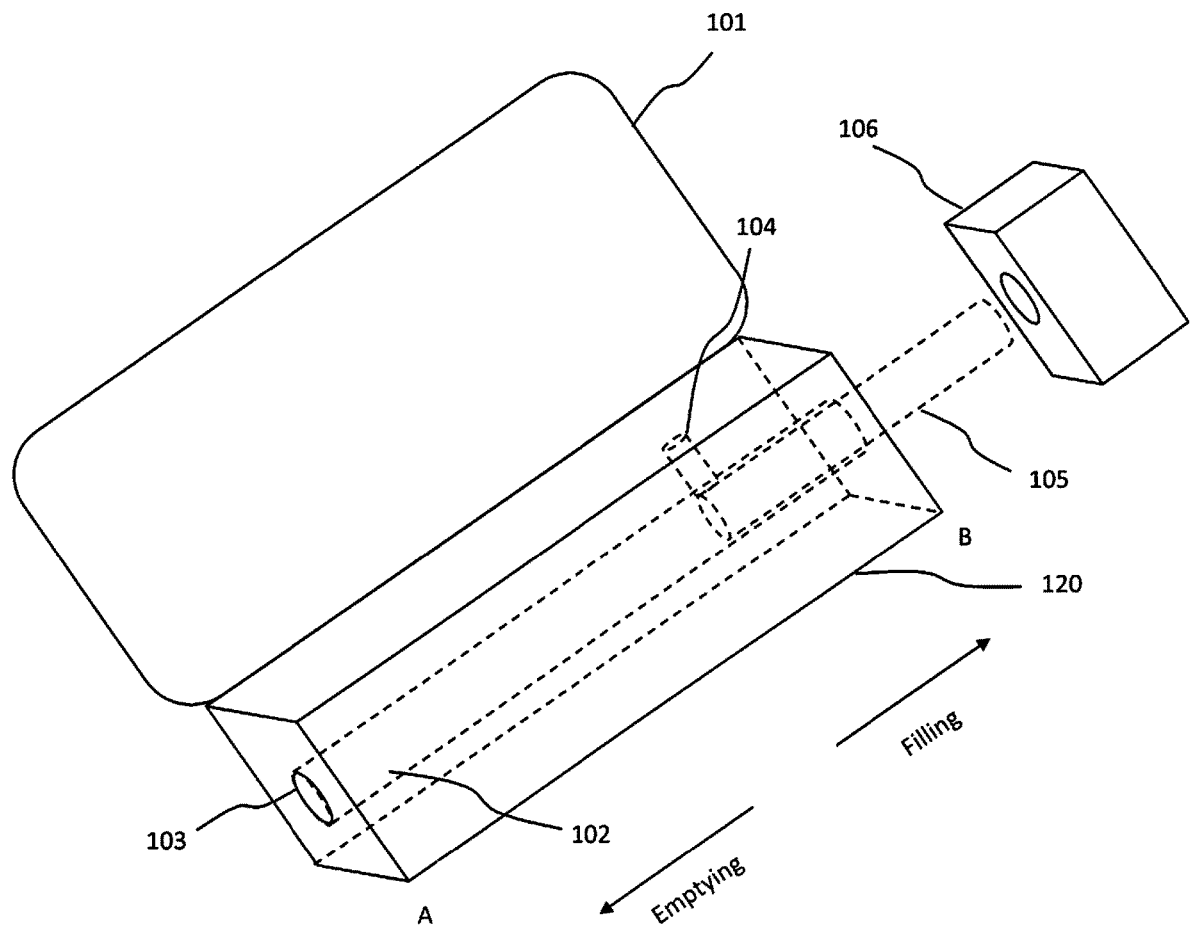
FIG. 1 is an illustration depicting a medical device in accordance with an embodiment of the present invention.

As shown in FIG. 1, an exemplary embodiments of the present invention includes a flexible reservoir 101 for housing a supply of a liquid drug, a rigid structure 120 with a chamber 102 and a side hole 104 in fluid communication with the flexible reservoir 101, and a plunger 105 mounted inside the chamber and configured to seal one side of the chamber 102. The term "flexible reservoir" includes reservoir structures that are both entirely flexible, such as collapsible fluid pouches or bladders, as well as reservoir structures that are only partially flexible by virtue of having both flexible and rigid wall portions. An exit/entrance 103 of the chamber 102 allows fluid in and out of the chamber 102. The plunger 105 is capable of moving in the axial direction of the chamber 102 from end A to end B for filling the chamber, or alternatively from end B to end A for emptying the chamber. The plunger 105 is positioned in the chamber 102 such that it prevents liquid from leaking out of the chamber 102. When the plunger 105 moves from end A to end B for filling, a fluid source is connected to end A. When the plunger 105 passes the side hole 104, fluid fills the chamber 102 and flows through the side hole 104 into the flexible reservoir 101 until the flexible reservoir 101 is filled. At the same time, a sensor 106 is triggered to transmit a volume signal. When the plunger 105 moves from end B to end A for emptying, the flexible reservoir 101 is emptied first. When the plunger 105 passes the side hole 104, the flexible reservoir 101 is emptied. The sensor 106 is triggered again to transmit another volume signal to indicate low fluid volume in the reservoir.

One of ordinary skill in the art will appreciate that medical device shown in FIG. 1 may be configured to be fully functional when the sensor 106 is an electrical switch. For instance, when the plunger 105 passes the side hole 104, an electrical signal is transmitted from the sensor 106 to indicate the volume information. The sensor 106 may also alternatively be implemented using an optical sensor. For instance, when the plunger 105 passes the side hole 104, an optical signal is transmitted from the sensor 106 to indicate the volume information. Alternatively, the sensor 106 may be implemented using a magnetic sensor.

When emptying the flexible reservoir 101, a pump or means can be arranged downstream of the flexible reservoir 101 and the chamber 102, to produce a negative pressure that conveys the fluid from the flexible reservoir 101 to its destination. When filling the flexible reservoir 101, similar means can be arranged to produce a positive pressure that conveys the fluid from another fluid source into the flexible reservoir 101 through the exit/entrance 103.

In one exemplary embodiment of the present invention, the sensor 106 is an electrical switch aligned with the end B of the chamber 102. The button or actuator 107 of the switch 106 is pointed toward the opening of the chamber 102. When the plunger 105 moves from end A to end B and passes the side hole 104, the end of the plunger 105 touches the button 107 of the electrical switch and triggers the switch 106 to transmit a volume signal. One of ordinary skill in the art will appreciate that additional supporting and housing structure may exist to support and house the above components.

Figure 2:
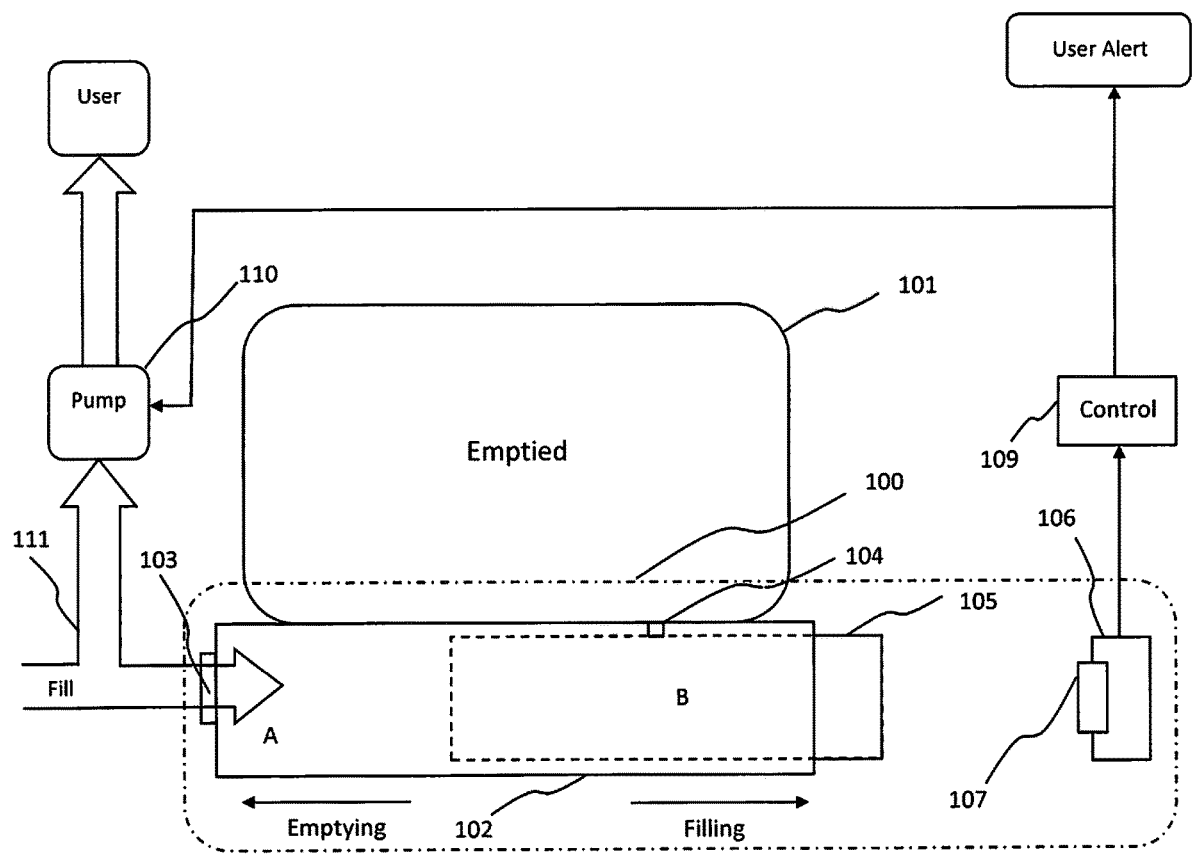
FIG. 2 is an illustration of the empty condition of the medical device of FIG. 1.

FIG. 2 is an illustration of the low volume state of the present invention with a pump mechanism. To empty the flexible reservoir 101, the pump mechanism 110 is located downstream of the flexible reservoir 101. The initial position of the plunger 105 is in position B. The pump mechanism produces a negative pressure on the fluid inside the chamber 102 and the flexible reservoir 101. Fluid inside the flexible reservoir 101 flows through the side hole 104 into the chamber 102, and through the chamber exit/entrance 103 to conduit 111 to the pump mechanism 110. The negative pressure causes the flexible reservoir 101 to be emptied first. When the flexible reservoir 101 is emptied, continued negative pressure from the pump mechanism 110 causes the plunger 105 to move from position B toward position A, and the button 107 on the switch 106 is activated to transmit a low volume signal to a control module 109. Control module 109 then sends a low-volume warning signal to the user.

Figure 3:
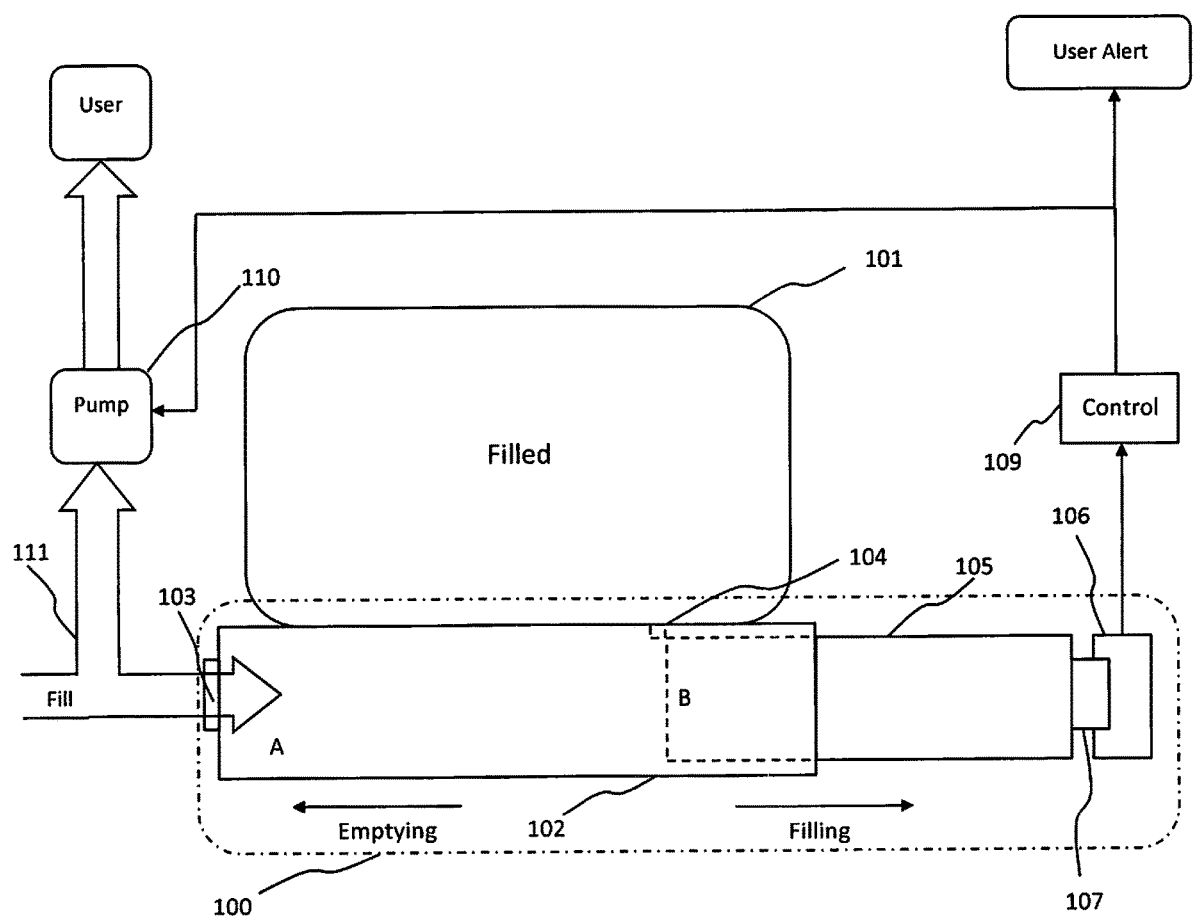
FIG. 3 is an illustration of the filled condition of the medical device of FIG. 1.

FIG. 3 is an illustration of the high volume state of the device of FIG. 2. To fill the flexible reservoir 101, a fill syringe or other device is used to forcibly inject fluid through a valve or seal into the exit/entrance 103. The initial position of the plunger 105 is position A. The plunger 105 is pushed back by the positive pressure inside the chamber 102 produced by the filling device. When the plunger 105 passes the side hole 104 in the chamber 102, fluid starts to flow into the flexible reservoir 101 through the side hole 104. When the flexible reservoir 101 is filled with fluid, the positive pressure increases and pushes the plunger 105 further back to position B to activate the button 107 on the switch 106 to transmit a high volume signal to the control module 109. Then the pump means 110 can be started to run at a pre-determined speed, the liquid in the flexible reservoir 101 will be pumped to the user and the flexible reservoir 101 will be emptied as illustrated in FIG. 2, when the sensor 106 will be activated to transmit a low liquid volume signal.

Figure 4:
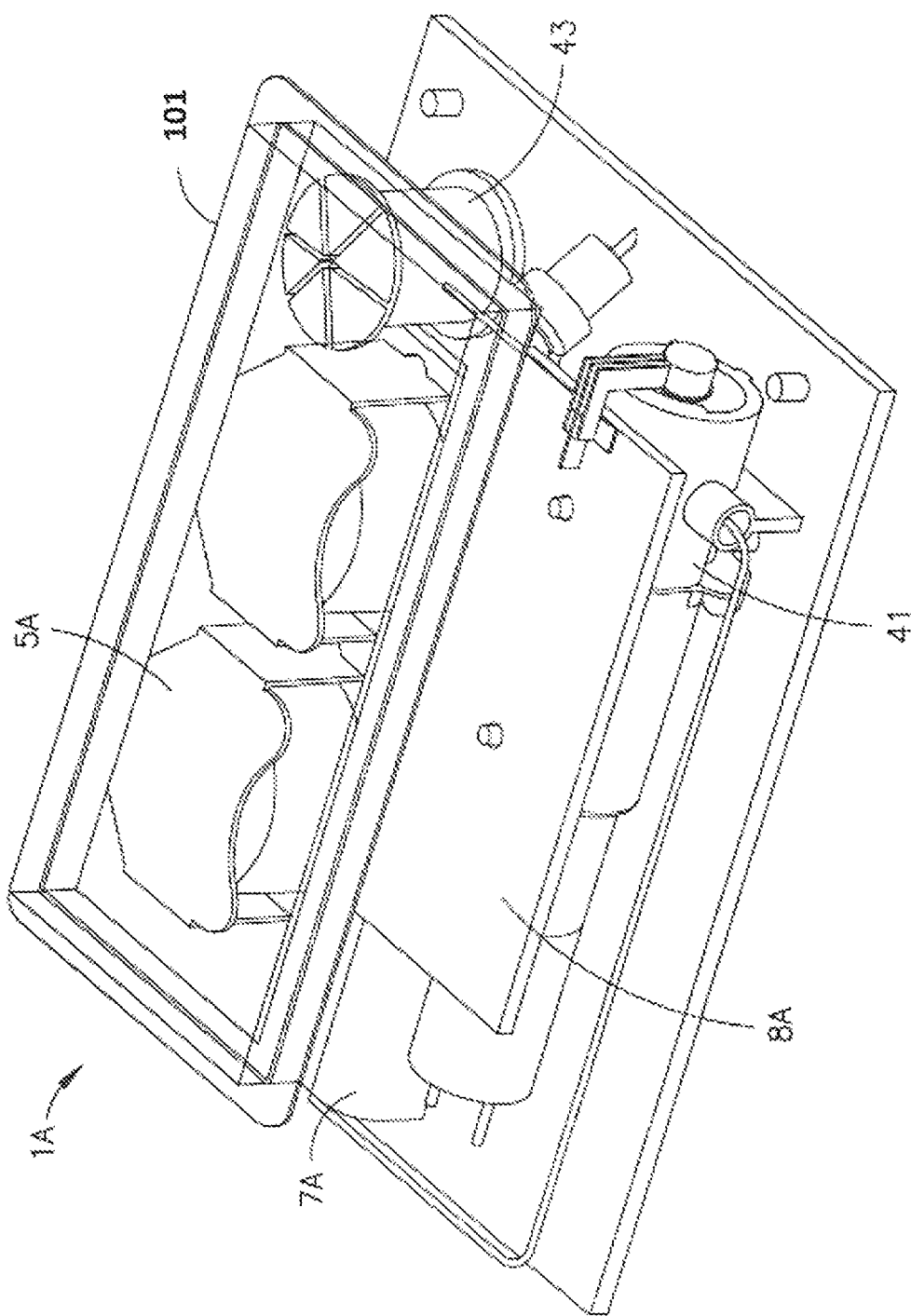
FIG. 4 is a perspective view of a flexible reservoir implemented in a patch pump system.

FIG. 4 is a perspective view of the flexible reservoir 101 implemented in a patch pump 1A illustrated without a cover. Such arrangement may further reduce the external dimensions of the patch pump 1A, with the flexible reservoir 101 filling voids within the patch pump 1A. The patch pump 1A is illustrated with a cannula insertion device 7A that inserts the cannula into the surface of a user's skin. The patch pump 1A further comprises a power source 5A in the form of batteries; a metering sub-system 41 that monitors the volume of insulin and includes a low volume detecting means; control electronics 8A for controlling the components of the device; and a reservoir fill port 43 for receiving a fill syringe 45 to fill the reservoir 101.

Figure 5:
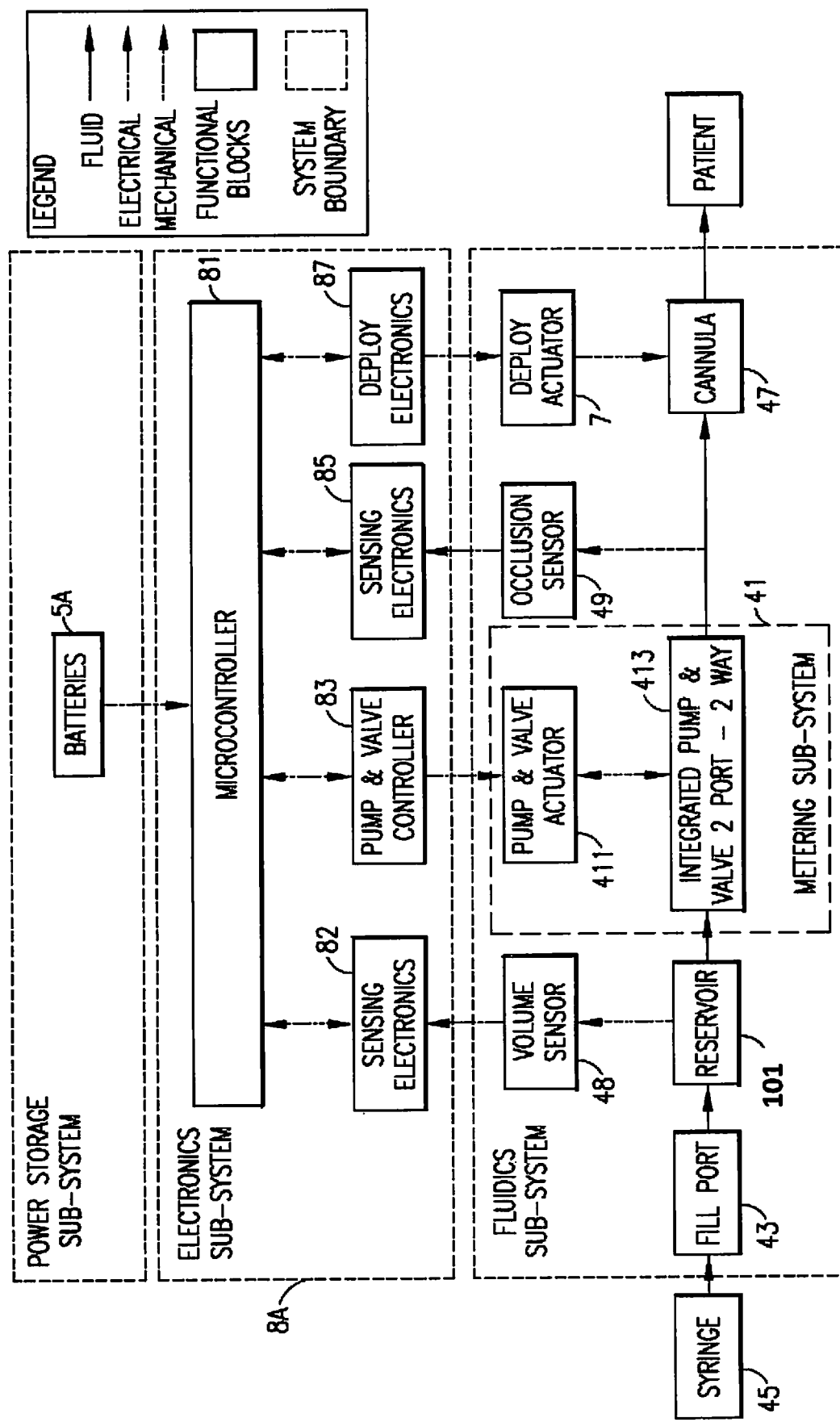
FIG. 5 is a fluidic architecture and metering sub-system diagram of the patch pump system of FIG. 4.

FIG. 5 is a fluidic architecture and metering sub-system diagram of the patch pump 1A of FIG. 4. The power storage sub-system for the patch pump 1A includes batteries 5A. The control electronics 8A of the patch pump 1A may include a microcontroller 81, sensing electronics 82, pump and valve controller 83, sensing electronics 85 and deployment electronics 87, that control the operation of the patch pump 1A. The patch pump 1A includes a fluidics sub-system that comprises the reservoir 101, a volume sensor 48 for the reservoir 101, and a reservoir fill port 43 for receiving a fill syringe 45 to fill the reservoir 4A. The fluidics sub-system may include a metering system comprising a pump and valve actuator 411 and an integrated pump and valve mechanism 413. The fluidics sub-system may further include an occlusion sensor 49, a deploy actuator or cannula insertion device 7, as well as a cannula 47 for insertion into an infusion site on the user's skin. In one embodiment of the present invention, the volume sensor is implemented with the sensor 106 of FIGS. 1, 2 and 3.

Figure 6:
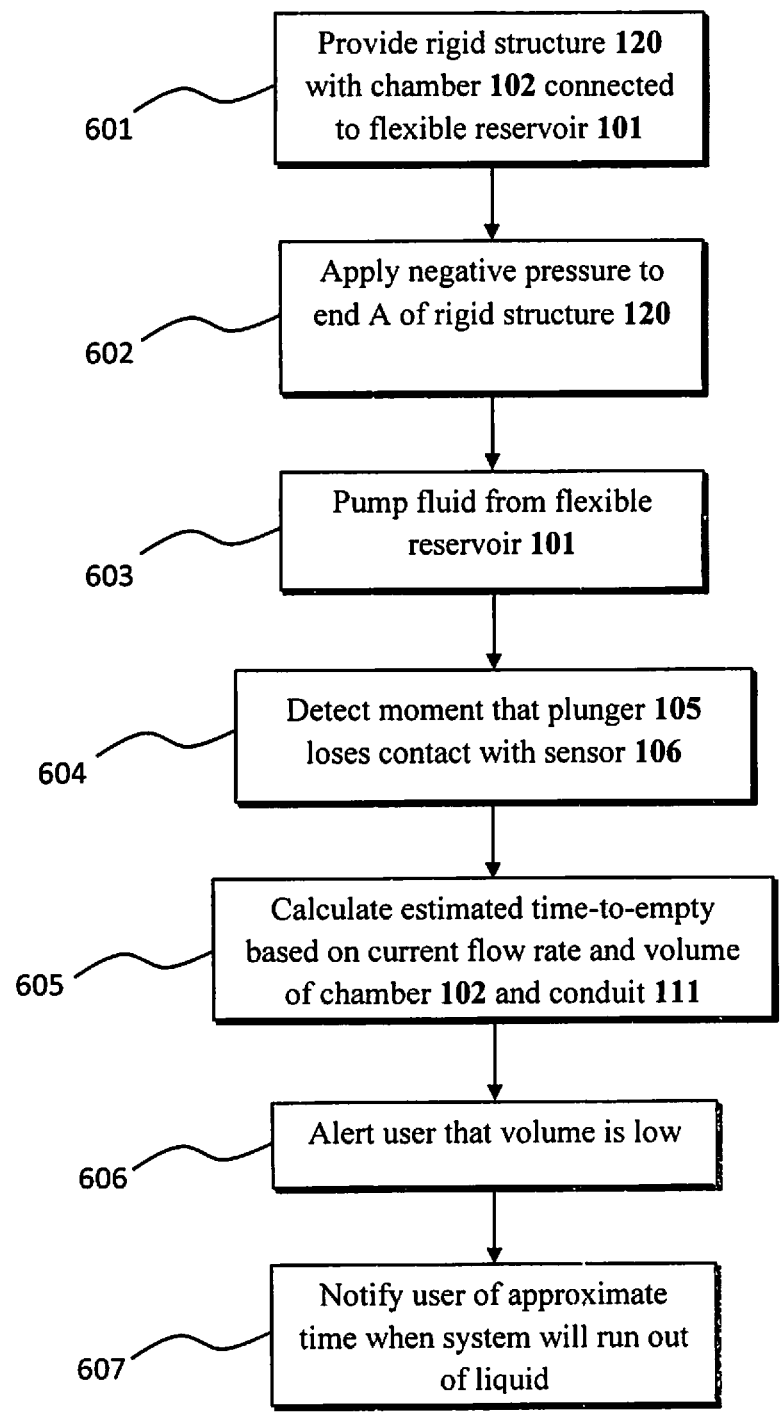
FIG. 6 is a flowchart illustrating a method for detecting low liquid volume and for notifying the user of estimated time-to-empty.

FIG. 6 is a flowchart illustrating the method for alerting the user of low liquid volume and for notifying the user of an estimated time-to-empty. In step 602, when the flexible reservoir 101 is emptied by the application of a negative pressure to end A of the chamber 102, fluid flows out of the flexible reservoir 101 and through the chamber 102. In step 603, this continues until all of the fluid is removed from the flexible reservoir 101. At this moment, the negative pressure will build until it is sufficient to cause the plunger 105 to slide forward in the chamber 102. When the plunger 105 begins to move, the back edge of the plunger 105 will lose contact with the button 107 of the switch, causing a low volume signal to be transmitted to the control module 109. In step 604, the moment that the plunger 105 loses contact with the button 107 of the switch 106 is detected. The exact volume remaining in the system at this moment is known since it is equal to the volume of the conduit 111 and the portion of the chamber 102 not occupied by the plunger 105. Dividing this volume by the current flow rate of the liquid, which is known from the operating speed of the pump mechanism 110, yields the estimated amount of time left before the system becomes empty of fluid in step 605. In step 606 the user of the system is alerted that the volume is low. If the flow rate is known, in step 607, the user can be notified of the approximate time that the system will run out of fluid.

One of ordinary skill in the art will appreciate that the features of the above exemplary embodiments may be similarly provided in a number of applications and are not limited to the above disclosure.

While the present invention has been shown and described with reference to particular illustrative embodiments, it is not to be restricted by the exemplary embodiments but only by the appended claims and their equivalents. It is to be appreciated that those skilled in the art can change or modify the exemplary embodiments without departing from the scope and spirit of the present invention.

What is claimed is:

1. A medical device for administering liquid drug therapy to a user with a low volume sensor, said medical device comprising:
   a flexible reservoir for containing a supply of a liquid drug;
   a rigid structure with a chamber and a side hole in fluid communication with the flexible reservoir;
   a plunger mounted inside the chamber and configured to seal one side of the chamber; and
   a sensor for detecting low liquid volume in the flexible reservoir, wherein:
   when the inside end of the plunger passes the side hole, the sensor is activated to transmit a signal indicating low liquid volume in the flexible reservoir.

2. The medical device of claim 1, wherein the sensor comprises an electrical switch.

3. The medical device of claim 2, wherein the electrical switch is triggered by a button.

4. The medical device of claim 1, wherein the sensor comprises an optical sensor.

5. The medical device of claim 1, wherein the sensor comprises a magnetic sensor.

6. The medical device of claim 1, further comprising a control module connected to the sensor for receiving the low liquid volume signal.

7. The medical device of claim 1, further comprising an alarm system for warning of a low liquid volume state of the reservoir.

8. The medical device of claim 7, wherein the alarm system transmits a light signal as a warning of low liquid volume in the reservoir.

9. The medical device of claim 7, wherein the alarm system transmits sound signal as a warning of low liquid volume in the reservoir.

10. The medical device of claim 7, wherein the alarm system transmits a vibrational signal as a warning of low liquid volume in the reservoir.

11. The medical device of claim 7, wherein the alarm system transmits a combined light, sound and/or vibration signal as a warning of low liquid volume in the reservoir.

12. The medical device of claim 1, further comprising a pump mechanism for pumping liquid out of the flexible reservoir.

13. A medical device for administering liquid drug therapy to a user with a liquid volume sensor, said medical device comprising:
   a flexible reservoir for containing liquid;
   a pump mechanism in fluid connection with the flexible reservoir for pumping liquid out of the flexible reservoir;
   a freely movable plunger in fluid communication with the flexible reservoir and the pump mechanism, the freely movable plunger moving only in response to liquid pressure and not forming a part of the pump mechanism;
   a sensor for detecting liquid volume inside the flexible reservoir by detecting a position or change in position of the freely movable plunger; and
   a control module in functional connection with the sensor for receiving a volume signal from the sensor.

14. A method for detecting low liquid volume and notifying a user of time-to-empty in a system comprising a pump mechanism, a flexible reservoir for housing a supply of a liquid drug, a rigid structure with a chamber and a side hole in fluid communication with the flexible reservoir, a plunger mounted inside the chamber and configured to seal one side of the chamber, a sensor for detecting low liquid volume in the flexible reservoir, and a control module in functional connection with the pump mechanism for controlling the operation of the pump mechanism, wherein when the inside end of the plunger passes the side hole, the sensor is activated to transmit a signal indicating low liquid volume in the flexible reservoir, the method comprising the steps of:
   providing the rigid structure with the chamber connected to the flexible reservoir;
   applying a negative pressure to end of the rigid structure;
   removing fluid from the flexible reservoir;
   detecting moment that the plunger loses contact with the sensor;
   calculating estimated time for empty based on current flow rate and volume of the chamber and the conduit;
   alerting the user that volume is low; and
   notifying user of an approximate time when the system will run out of liquid.

\* \* \* \* \*